United States Patent [19]
Van der Gaast

[11] 3,964,674
[45] June 22, 1976

[54] MENSTRUAL CYCLE CALCULATOR

[76] Inventor: Harry Van der Gaast, 289 N. Hibiscus Drive, Miami Beach, Fla. 33139

[22] Filed: May 9, 1975

[21] Appl. No.: 576,047

[52] U.S. Cl. .............................. 235/88 RC; 58/4 M
[51] Int. Cl.² ...................... G06C 3/00; G04B 19/24
[58] Field of Search .................. 58/4 M; 235/88 RC

[56] References Cited
UNITED STATES PATENTS

| | | |
|---|---|---|
| 3,278,118 | 10/1966 | Klein, Jr. ........................ 235/88 RC |
| 3,534,905 | 10/1970 | Kull ................................ 235/88 RC |

*Primary Examiner*—Edith Simmons Jackmon

[57] ABSTRACT

A menstrual calculator to determine the fertile dates of a period composed of a base panel and dials and a pointer which bear date indicia and are rotatable independently about a common dial pin.

2 Claims, 6 Drawing Figures

MENSTRUAL CYCLE CALCULATOR

FIELD OF THE INVENTION

This invention relates to a manually operable calcultor for use in predicting the fertile days in a woman's menstrual cycle for the purposes of conception control.

BACKGROUND OF THE INVENTION

As is perhaps known, women have determinable period cycles which, once determined, whether regular or irregular in length, may be used to provide a basis for predicting the days within the next menstrual period which are fertile. In other words, by knowing the length of a menstrual period and by taking into consideration whether the user of the calculator is regular or irregular, and the date on which a period commenced and the number of days of the month it commenced, one is able to predict the dates between which a person is fertile. This invention is of a calculator which provides a simple and inexpensive device whereby a user may determine the dates between which the fertile portion of a cycle occurs.

Generally speaking, it is an object of this invention to provide a calaculator which provides a base panel and dials and a pointer which are each rotatable on a common dial pin so that the dials which carry indicia, as does the base, can be adjusted relative to one another to reflect particular information about the user, i.e., whether regular or irregular, the date on which the period commenced, so that the dates of the fertible portion of the period are calculated.

In accordance with these and other objects which will become apparent hereinafter the instant invention will now be described with reference to the accompanying drawings in which:

DESCRIPTION OF THE PREFERRED EMBODIMENT

Figure 1:
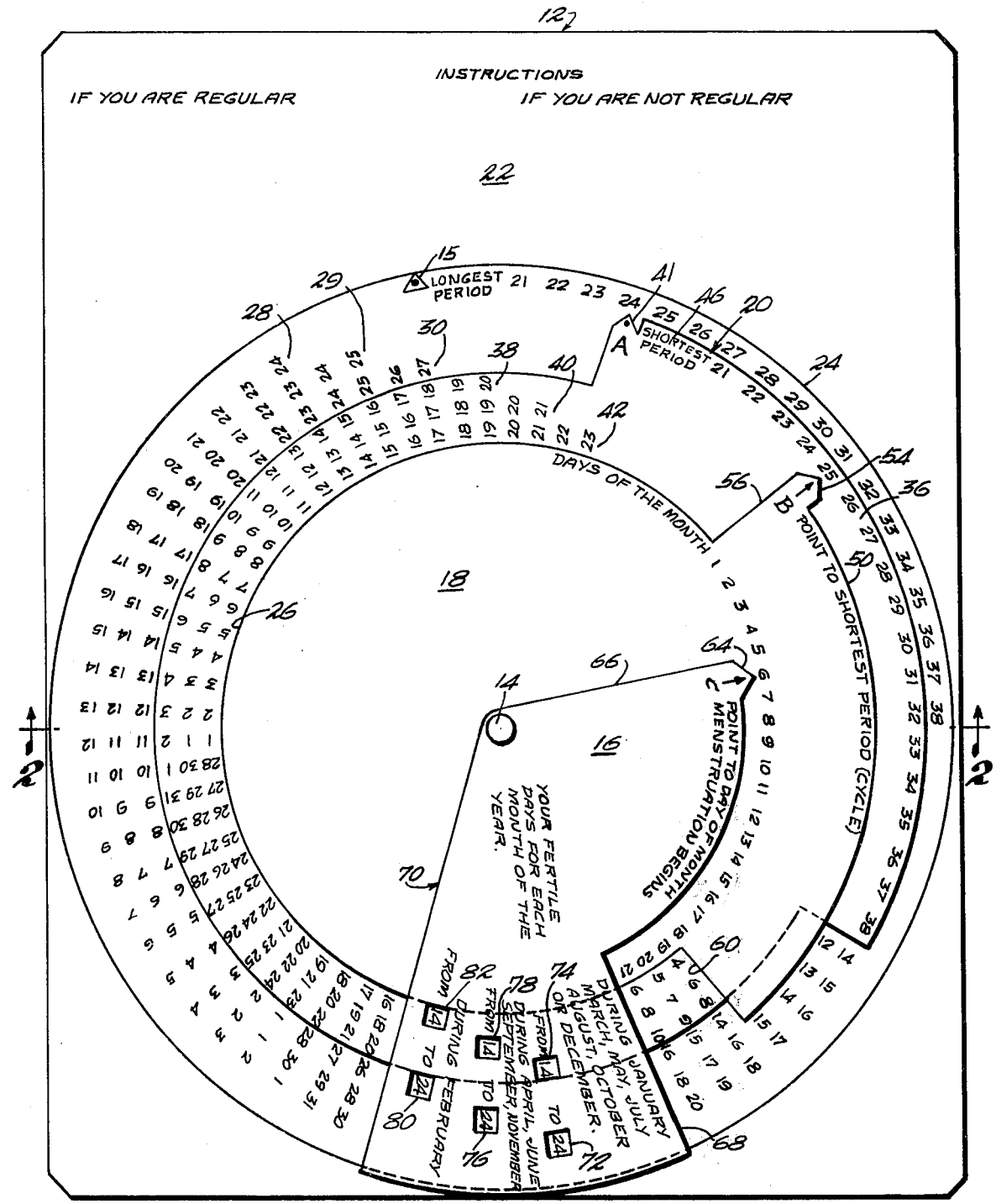
FIG. 1 is a view of the calculator and illustrating an adjustment of the dials for calculating the fertile portion of an irregular period.
Figure 2:
FIG. 2 is a view in cross section taken on the plane indicated by line 2—2 of FIG. 1.

Referring to the drawings wherein like reference characters designate like or corresponding parts throughout the several views, there is shown in FIGS. 1 and 2 the calculator which is designated by the numeral 12. It includes a center pivot or dial pin 14 and rotatably mounted to the pin there are provided a pointer and reader member 16, a first dial 18, a second dial 20, and a base panel 22. Generally, the calculator is used to tell a person the fertile days of the month.

In the event that the person using the calculator has a regular menstrual period, i.e., the same number of days between the start date of each period, the operation is as follows: the second dial 20 is rotated into registry with the base panel, that is it is rotated until the numerals of a period scale 36 on the outer edge of the second dial are in corresponding angular position with respect to the same numerals of a period scale 24 on the outer portion of the base panel, i.e., the pointer 41 adjacent the notation "shortest period" 46 is immediately, radially, inwardly from the pointer 15 adjacent the notation "longest period" 34 on the base panel; thereafter, with the base panel and second panel being held together, the first dial 18 is moved so that the arrowed line B 54 of the first dial points radially outwardly to the figure of the period scale which represents the number of days which are in a regular cycle of the user; finally, the pointer C 64 of the pointer means 16, is rotated to point to the day of the month on a date scale 52 on the first dial 18 that corresponds to the date of the month on which the user's period commenced. When the calculator has been thus manipulated, the reader means portion 70 is referred to where, through the windows, 72, 74; 78, 78', or 80, 82 one can read on a radial line the dates between which the person is fertile selecting the pair of windows which corresponds to the number of days that are in the calendar month in which the period commenced, i.e., a 31-day month, 30-day month or 28-day February month.

In the event that the person using the calculator has an irregular menstrual period, i.e., the number of days between the start date of periods varies, the operation is as follows: the second dial 20 is rotated relative to the base panel such that the pointer 41 points to the number of the period scale 24 which corresponds to the number of days of the longest period experienced by the user; thereafter, with the base panel and second dial held together, the first dial is rotated until the arrowed line B 54 points radially outwardly to the figure of the period scale 36 on the second dial which corresponds to the number of days in the shortest period experienced by the user; thereafter, the pointer C 64 of the pointer and reader means 16 is rotated to point the number which corresponds to the day of the month that the period commenced and the reader means portion is then referred to where, through the appropriate pair of windows, one can read the dates between which the user is fertile.

Generally the base panel and dials are divided by 72 equi-angularly spaced radial lines emanating outwardly from the centerline of the pivot means.

Referring to the base panel 22, shown in FIG. 1, it is provided with two separate instructions adjacent a pattern of numerals to be described. The instructions are to be followed by the user depending on whether that person has a normal or irregular length period. The instructions in the preferred embodiment are printed under two separate headings: one under the heading "If You Are Regular" and the other under the heading "If You Are Not Regular."

Figure 3:
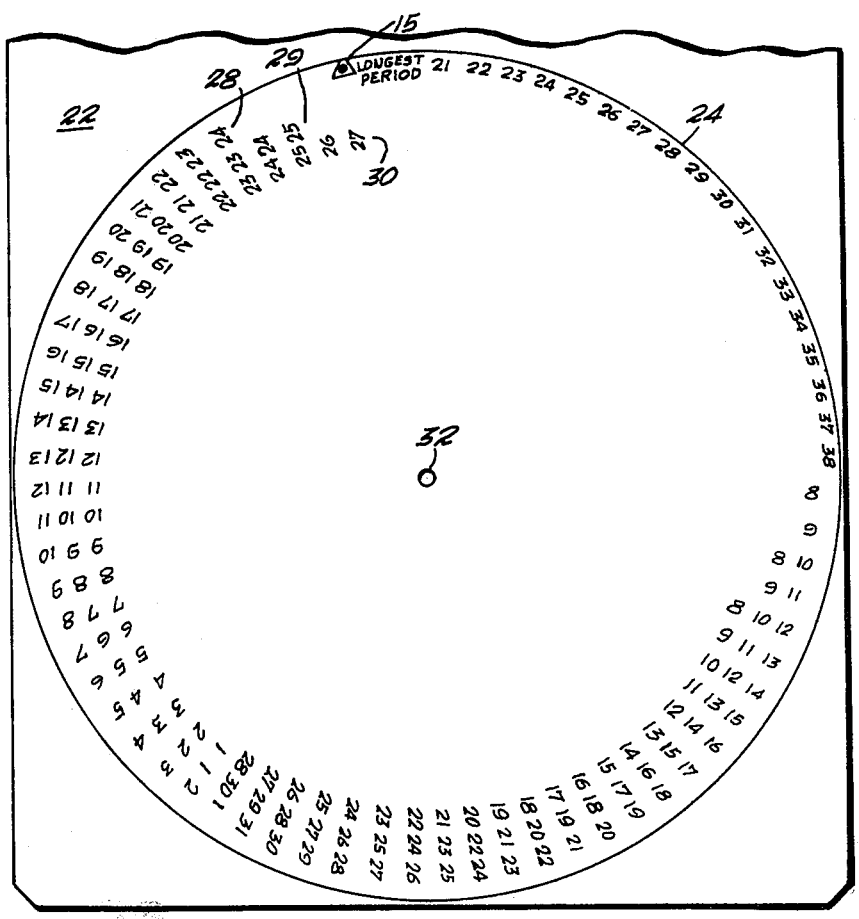
FIG. 3 is a partial view of the base panel 22 of FIG. 1.

With more particular reference to the base panel it will be convenient to refer to FIG. 3. A hole 32 is provided for passage of the dial pin 14. On an outer arcuate portion, a period scale 24 is provided which is composed of a plurality of equi-angularly spaced cardinal numeral figures in progressively increasing order defining scale units within the range between 20 and 40, each figure representing a different length commonly encountered menstrual period.

Spaced radially inwardly from and adjacent to the period scale 24 there is a circular strip portion which will now be described. This circular strip portion carries indicia defining three separate scales, designated by the numerals 28, 29 and 30, respectively, an outer, intermediate and inner scale path. In each, the indicia are equi-angularly spaced cardinal numeral figures in progressively increasing order in the adjacent scale units and each represent a date of a month. Three scales are required to take into consideration the variables of: a 31-day month, as does the outer scale, a 30-day month, as does the intermediate scale, and a 28-day month, as does the inner scale.

Figure 4:
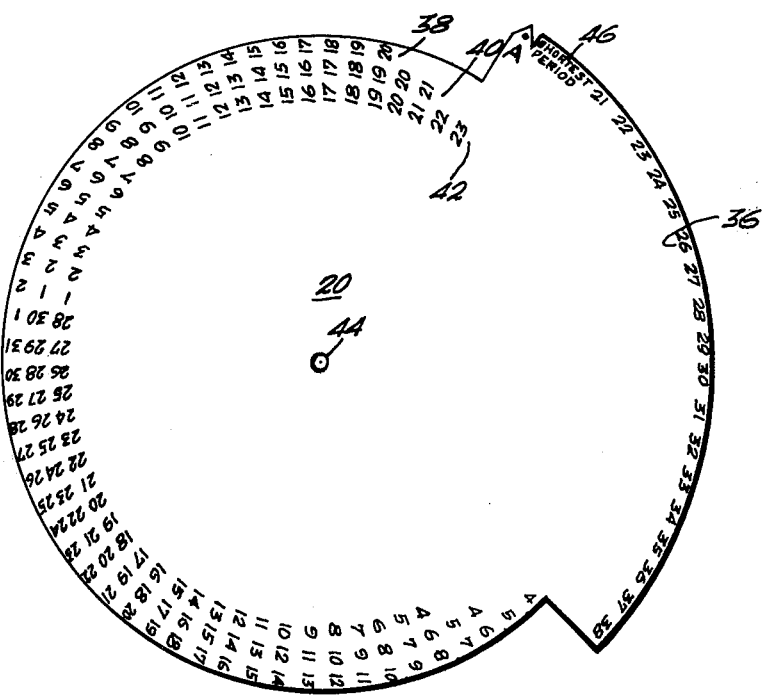
FIG. 4 is a plan view of a dial indicated by the numeral 20 in FIG. 1.

Referring to the second dial, it will be convenient to refer to FIG. 4. A central hole 44 is provided to accommodate the pin 14 for movement of rotation of the second dial 20. The second dial is circular with the exception that it includes an arcuate segment 46 of the radius of curvature less than the radius of the period scale 24 and greater than the radius of the outer path 28 of the base. On the marginal edge of the arcuate segment a second period scale 36 is provided composed of a plurality of equi-angularly spaced cardinal number figures in progressively increasing order defining scale units within the range between 20 and 40 and each figure representing a different length commonly encountered menstrual period. The second dial also includes a circular strip portion on which indicia define three scales, 38, 40 and 42, that is an outer, intermediate and inner path each of which are circular and are provided with cardinal numeral figures representing a date of a month in progressively increasing order, three scales being required to take into consideration the variables of a 31-day month, as does the outer scale 38, a 30-day month, as does the intermediate scale 40, and the month of February which has 28 days as does the scale 42. The radius of the outer scale is slightly less than the radius of the inner scale 30 of the base panel.

The scales of the month dates of the base panel and of the second dial represent the longest period and the shortest period respectively and their relative adjustment by rotation of the second panel adjusts for the reading of the fertile period.

Figure 5:
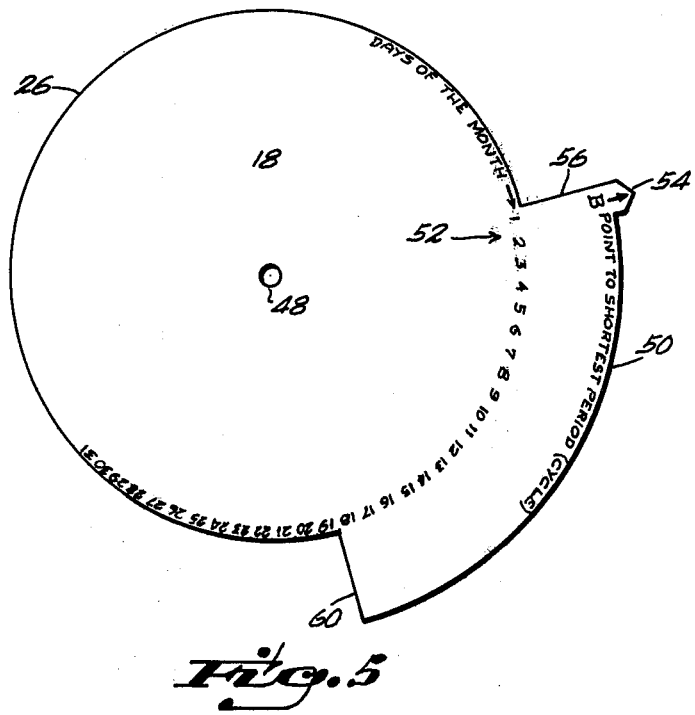
FIG. 5 is a view of a dial indicated by the numeral 18 in FIG. 2.

Referring to FIG. 5, the first dial is shown. This dial 18 is provided with a central hole 48 to accommodate the pin and is circular as defined by the line 26 with the exception that it includes an arcuate portion 50 of a radius of curvature greater than the radius of curvature of the outer path 38 of the second dial and less than the radius of curvature of the period scale 46 of the second dial and of the inner path 30 of the base panel. Along the margin of the edge 50 a pointer 54 is provided adjacent the radial edge 56. A concentric circular scale 52 of dates commencing with the numeral 1 and terminating with the numeral 31 is provided as indicated in FIG. 5 defining a date scale to indicate the date on the month on which the user's period commenced.

Figure 6:
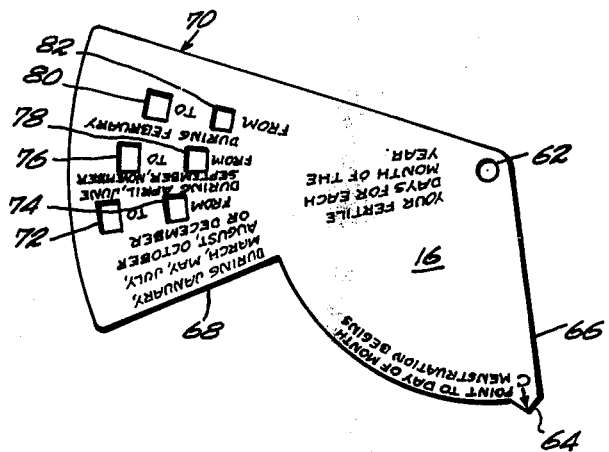
FIG. 6 is a view of the pointer and reader means indicated by the numeral 16 in FIGS. 1 and 2.

The pointer and reader means will best be understood on reference to FIG. 6. It includes a pointer 64 of a radius slightly less than the radius of the date scale on the first dial and a reader means which is fixed to it and angularly spaced and which reader means is a panel of an outer radius between the edges 68 and 70 which is greater than the radius of the outer path 28 of the base panel and the reader portion includes a first pair of windows 72 and 74 which are radially aligned and adapted to overlay the figures of the outer path 28 and 38 respectively of the base panel and second dial and windows 76 and 78 which are adapted to overlay the figures of the intermediate paths 29 and 40 and a third pair of windows 80 and 82 which are adapted to overlay the numerals of the path 30 and 42.

What is claimed is:
1. A calculator for computing menstrual cycles comprising:
A. a base panel, a first dial, a second dial, and a pointer and reader member, and dial pin means connecting said base, dials and pointer member for rotation about a common center and relative to said base panel, and said panel, dials and member having indicia arranged thereon in equi-angularly spaced scale units about said dial pin,
B. said base panel having:
  indicia arranged in an outer arcuate strip portion defining a period scale composed of a plurality of equiangularly spaced cardianal number figures in progressively increasing order each figure being in a separate adjacent scale unit within the range of about 20 and 40 and each figure representing a different length, commonly encountered, menstrual period, and
  indicia arranged in an inner circular strip portion adjacent said arcuate strip portion and the indicia on said circular strip portion defining concentric adjacent inner, outer and intermediate circular paths,
  each said path defining a separate month scale composed of a series of equi-angularly spaced cardinal number figures each in an adjacent separate scale unit in progressively increasing order and each of said month scales being angularly spaced with respect to said period scale a predetermined number of scale units,
C. said first dial being circular and of a radius less than that of the inner path of said base panel and said first dial having an arcuate segment of a radius of curvature greater than the radius of the outer path of said base panel and less than the radius of the outer arcuate strip portion of said base panel, said arcuate segment of the said first dial having
  indicia arranged in an outer arcuate strip portion defining a second period scale composed of a plurality of equi-angularly spaced cardinal number figures in progressively increasing order each figure being in a separate adjacent scale unit within the range of about 20 to 40 and each figure representing a different length commonly encountered menstrual period, and
  indicia arranged in an inner circular strip portion adjacent said arcuate strip portion and the indicia on said circular strip portion defining concentric adjacent inner, outer and intermediate circular paths,
  each said path defining a separate month scale composed of a series of equi-angularly spaced cardinal number figures each in an adjacent separate scale unit in progressively increasing order and each of said month scales being angularly spaced with respect to said period scale a predetermined number of scale units, and
  a pointer means on said second dial to be positioned so as to point toward a figure in the period scale of the base panel to indicate the longest length of period experienced by the user,
D. a second generally circular dial of a radius less than the diameter of the first dial and having a days of the month scale composed of a series of numbers in a circular path said numbers being in progressive order and including the numerals 1 and 31 comprising a calendar scale representing the days of a month and said second dial including a pointer to be positioned so as to point toward a figure in the period scale of the second dial to indicate the shortest period experienced by the user, and E. a pointer and reader member having a pointer to point to the day in the calendar scale corresponding to the date of the month on which the period of the user commenced and a reader segment at a predetermined fixed angular distance from said second pointer means and extending radially outwardly and over said paths for use in reading the figures on the paths.

2. The calculator as set forth in claim 1 wherein said reader segment includes a first, second and third pair of windows, the windows of said first pair being at a radial position spaced from the dial pin a distance such that the outer paths of the first dial and base panel are visible therethrough, the windows of said second pair being at a radial position spaced from the dial pin a distance such that the intermediate paths of the first dial and base panel are visible therethrough, and the third pair being at a radial position spaced from the dial pin a distance such that the inner paths of the first dial and base panel are visible therethrough.

* * * * *